(12) United States Patent
Lagmanson

(10) Patent No.: US 11,568,636 B2
(45) Date of Patent: Jan. 31, 2023

(54) REFLECTIVE CABLE LOCATING SYSTEM

(71) Applicant: ADVANCED GEOSCIENCES, INC., Austin, TX (US)

(72) Inventor: Markus Lagmanson, Austin, TX (US)

(73) Assignee: ADVANCED GEOSCIENCES, INC., Austin, TX (US)

( * ) Notice: Subject to any disclaimer, the term of this patent is extended or adjusted under 35 U.S.C. 154(b) by 10 days.

(21) Appl. No.: 16/860,787

(22) Filed: Apr. 28, 2020

(65) Prior Publication Data

US 2020/0349338 A1 Nov. 5, 2020

Related U.S. Application Data

(60) Provisional application No. 62/841,976, filed on May 2, 2019.

(51) Int. Cl.
| | |
|---|---|
| *G06T 11/60* | (2006.01) |
| *G06V 10/60* | (2022.01) |
| *G06V 20/13* | (2022.01) |
| *G06V 10/42* | (2022.01) |

(52) U.S. Cl.
CPC .............. *G06V 20/13* (2022.01); *G06T 11/60* (2013.01); *G06V 10/42* (2022.01); *G06V 10/60* (2022.01)

(58) Field of Classification Search
None
See application file for complete search history.

(56) References Cited

U.S. PATENT DOCUMENTS

| | | | | |
|---|---|---|---|---|
| 4,875,215 A | * | 10/1989 | Hughes | H01S 3/06754 372/6 |
| 4,902,126 A | * | 2/1990 | Koechner | G01S 17/04 356/5.08 |
| 5,576,973 A | * | 11/1996 | Haddy | G01V 3/15 342/357.25 |
| 5,577,147 A | | 11/1996 | Arroyo et al. | |
| 6,995,565 B1 | | 2/2006 | Tulloch et al. | |
| 8,254,660 B2 | | 8/2012 | Verreet | |
| 8,958,671 B2 | | 2/2015 | Cofre Luna et al. | |

(Continued)

FOREIGN PATENT DOCUMENTS

| | | |
|---|---|---|
| RU | 2258204 C1 | 8/2005 |
| WO | WO 2018176071 A1 | 10/2018 |

OTHER PUBLICATIONS

PCT International Search Report and Written Opinion, PCT/US2020/031135, dated Aug. 6, 2020.

*Primary Examiner* — David H Chu
(74) *Attorney, Agent, or Firm* — Haynes and Boone, LLP

(57) ABSTRACT

A reflective cable system for a geophysical survey system includes a reflective cable that includes a conductive wire surrounded by an electrically insulating sheath and an exterior surface. The reflective cable includes reflective material that is on or visible through the exterior surface and that is configured to reflect a complete spectrum of light provided by a light source back to the light source. The reflective cable system also includes a connector electrically coupled to at least one end of the reflective cable and configured to couple to a geophysical survey system. The reflective cable may be used to locate the reflective cable in a physical environment and used to determine a position of the reflective cable using lidar or photogrammetry for generating geophysical survey models.

20 Claims, 10 Drawing Sheets

(56) References Cited

U.S. PATENT DOCUMENTS

| | | | |
|---|---|---|---|
| 9,343,200 B2 | 5/2016 | Perez-Sanchez et al. | |
| 9,389,265 B2 | 7/2016 | Stephan et al. | |
| 9,681,033 B2 | 6/2017 | McCall et al. | |
| 9,778,097 B2 | 10/2017 | McEwen-King | |
| 2002/0060783 A1* | 5/2002 | Aoyama | G05D 1/0248 356/3.01 |
| 2005/0159929 A1* | 7/2005 | Overby | G01V 15/00 702/189 |
| 2006/0228003 A1* | 10/2006 | Silverstein | G01S 17/04 382/115 |
| 2006/0293837 A1* | 12/2006 | Bennett | G09B 29/003 701/532 |
| 2008/0079723 A1* | 4/2008 | Hanson | G06K 9/0063 345/427 |
| 2012/0116819 A1* | 5/2012 | Hertenstein | G06Q 40/08 705/4 |
| 2015/0211931 A1 | 7/2015 | Wang et al. | |
| 2015/0341619 A1 | 11/2015 | Meir et al. | |
| 2016/0023761 A1* | 1/2016 | McNally | H02G 1/02 29/407.01 |
| 2018/0247735 A1* | 8/2018 | Dalbe | H01B 13/148 |

\* cited by examiner

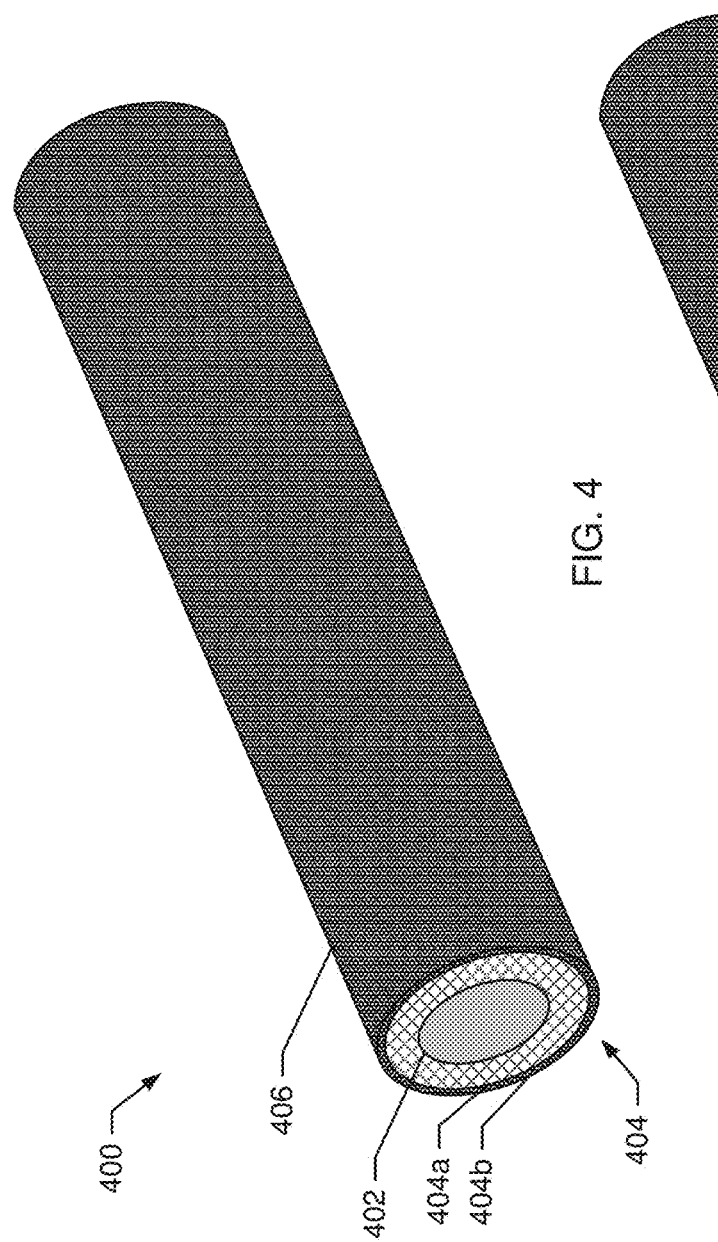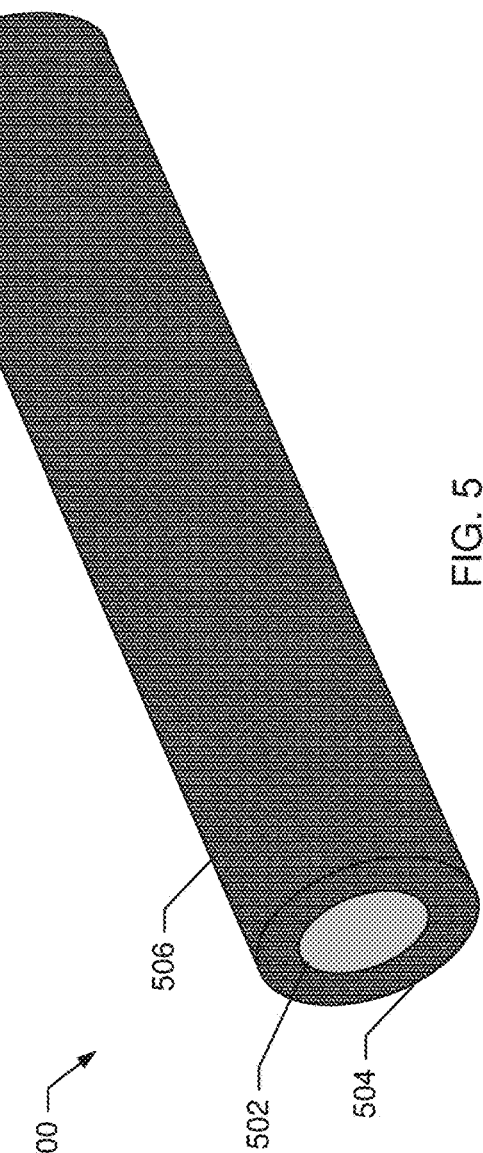

REFLECTIVE CABLE LOCATING SYSTEM

CROSS-REFERENCE TO RELATED APPLICATIONS

The present application claims benefit, under 35 U.S.C. 119(e), of U.S. Provisional Application No. 62/841,976, filed May 2, 2019. Each of the foregoing applications are incorporated by reference herein.

FIELD OF THE DISCLOSURE

This disclosure relates generally to geophysical surveys, and, more particularly, to locating a reflective cable for geophysical survey applications.

BACKGROUND

Various geophysical applications utilize electrical surveys to determine a sub-ground resistivity distribution by making electrical measurements on the ground. From such measurements, the resistivity of the sub-ground may be estimated and related to various geological parameters such as mineral and fluid content, porosity, and water saturation.

Resistivity measurements are typically made by applying current directly into the ground using a pair of transmitting electrodes. Resulting potential differences may then be measured directly using several other receiving electrodes. The receiving electrodes are typically arranged in an array or grid and coupled together by transmitting and receiving cables. Because the electrodes and cables are often deployed in remote locations that may include vegetation, in subterranean environments with little or no light, at night or other low light times of the day, and/or in water, locating the cables to move or retrieve is often difficult. Also, in some geophysical applications, it is important to know a precise geolocation of the cable. For example, when performing various types of geophysical surveys (e.g., electromagnetic (EM) methods), these surveys use electrical current bearing cables to induce Eddie currents, and thus knowing the location of cables can be used to generate accurate geophysical survey models.

SUMMARY

Systems and methods have been provided for locating and determining a position of a reflective cable in a physical environment.

In various embodiments of the methods and systems disclosed herein, a method of locating a reflective object is described. The method includes a computing device receiving a first image of a physical environment that includes a reflective object. The first image is captured by an imaging sensor at a first position and a first orientation when a first quantity of light from a light generator illuminates the physical environment during the capture of the first image by the imaging sensor. The computing device receives a second image of the physical environment that includes the reflective object that was captured by the imaging sensor at the first position and the first orientation when a second quantity of light from the light generator that is less than the first quantity of light illuminates the physical environment during the capture of the second image by the imaging sensor and compares the second image to the first image to generate a compared image. The compared image illustrates a difference in illuminance of the reflective object that distinguishes the reflective object from other objects in the physical environment.

In various embodiments of the methods and systems disclosed herein, a method of determining position of a reflective cable is described. The method includes imaging, by a cable locator device, a physical environment that includes a reflective cable, wherein the cable locator device includes an imaging sensor that detects light, and wherein one or more distances from the cable locator device to the reflective cable are calculated from the imaging; and determining one or more positions of the reflective cable based on the one or more distances and a position of the cable locator device.

In various embodiments of the methods and systems disclosed herein, A reflective cable system for a geophysical survey system is described. The reflective cable system includes a reflective cable including a conductive wire surrounded by an electrically insulating sheath and an exterior surface. The reflective cable includes reflective material that is on or visible through the exterior surface and that is configured to reflect a complete spectrum of light provided by a light source back to the light source. Also, a connector electrically is coupled to at least one end of the reflective cable and configured to couple to a geophysical survey system.

BRIEF DESCRIPTION OF THE DRAWINGS

FIG. 4 is a perspective view illustrating an embodiment of a reflective cable of the geophysical survey system of FIG. 3.

FIG. 5 is a perspective view illustrating an embodiment of a reflective cable of the geophysical survey system of FIG. 3.

Embodiments of the present disclosure may be understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

Figure 1:
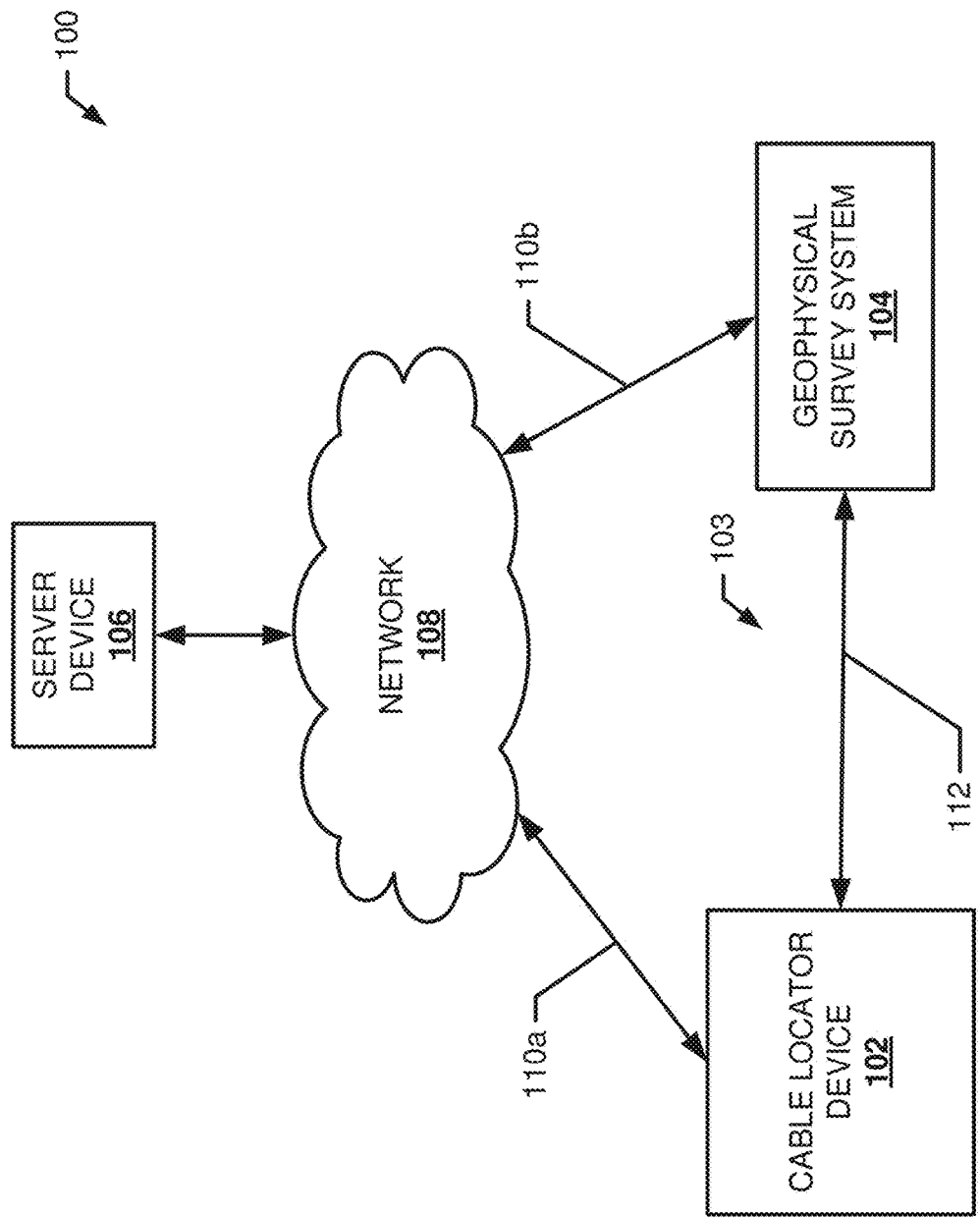
FIG. 1 is a schematic view illustrating an embodiment of a reflective cable locating system.

Embodiments of the present disclosure include reflective cable locating systems and methods that may be used, for example, to locate a cable on a surface of a physical environment. As discussed above, locating a cable used in geophysical applications may be difficult due to the environment and/or time of day that the cables are being deployed or retrieved in the environment. Furthermore, even if the cable is locatable by a user, some geophysical survey applications require that a position of the cable be determined. For example, the cables for geophysical sensors (e.g., geophones, magnetic sensors, ground penetrating radar antennas, electrodes, transmitter and receiver loops used in induced magnetic field measurements, temperature sensors, Internet of Things (IoT) sensors, and/or other geophysical sensors that would be apparent to one of skill in the art in possession of the present disclosure) may cause negative Induced Polarization (IP) decay when conducting geophysical surveys. Thus, a more accurate DC resistivity inversion model can be created by taking into account the position of cables when generating a DC resistivity inversion model or other geophysical survey models. Furthermore, many other geophysical surveying models may benefit from knowing the position of cables. For example, in electromagnetic (EM) methods, an electrical current bearing cable may induce Eddie currents and those currents are important to model accurately. Modeling those currents accurately requires knowing the position of cables.

Conventional positioning of a cable or determining a position of a cable often requires surveying equipment, tape measures, and/or a very accurate global positioning system (GPS). A technician can use this equipment to position the geophysical sensors on the ground of the physical environment as well as position or obtain the position of the cables that are coupled to the geophysical sensors. However, these systems require specialized knowledge, are difficult to maneuver and use in the field, expensive, and/or do not produce the position accuracy needed to generate accurate computer models of the sub-ground using the geophysical sensors. For example, tape measures are time consuming to deploy due to obstacles like boulders, trees, and other structures and inaccurate due to stretching and contracting caused by the ambient temperature. GPS by itself is only accurate to a couple of meters. Differential GPS is accurate but very expensive and requires specialized knowledge. Land surveying using a theodolite to survey geolocated points starting with a nearby United States Geological Survey (USGS) position marker is accurate but requires professional knowledge, is time consuming, and bulky to move around on terrain.

Photogrammetry methods using software (e.g. photogrammetry software from Pix4D™ of Lausanne, Switzerland) have been used with some mixed success in locating and determining position of objects and cables. The photogrammetry method requires identification of common objects in multiple photos. The accuracy is limited to the resolution of the camera's Charge-Coupled Device (CCD) and the ability to detect the cable in the image frame. A lidar (e.g., Light Imaging, Detection And Ranging (LIDAR)) method utilizes a laser ranging device that calculates the distance to an object (e.g., a cable) by transmitting a laser and measuring laser light travel time to and from the object. Lidar does this many hundreds of thousands of times per second to build up a three-dimensional point cloud of reflections. However, observing a thin cable in an environment using lidar is difficult as the strength of reflection is important as materials that absorb the laser light do not provide good backscattering, which is required for a distance calculation in determining a position of the cable.

The systems and methods of the present disclosure provide for locating a reflective cable for geophysical surveys in a physical environment as well as determining a position of the reflective cable in the physical environment. A geophysical survey system for a geophysical application may include a reflective cable system that includes a reflective cable having a conductive wire surrounded by an electrically insulating sheath that includes a reflective sheath portion that visible through or disposed on an exterior surface of cable. For example, the reflective sheath portion may include a reflective material such as a plurality of orthogonal 3-planar prisms and/or microspheres that are on or visible through the exterior surface and that are configured to reflect light provided by a light source back to the light source. For example, if the light source provides a full spectrum of visible light, the reflective material may reflect the full spectrum of visible light back to the light source. In other examples, a partial spectrum of light provided by the light source may be reflected back by the reflective material such that that partial spectrum is reflected. The reflective material may be configured to ensure that a maximum amount of backscattered light is directed 180 degrees back to the light source that may be, for example, the flash from a camera in photogrammetry applications or a laser pulse from a lidar unit in lidar applications. Also, the reflective sheath portion may be used by the user to locate the reflective cables in physical environments with low ambient illuminance as the user may be able to use a flashlight or headlamp to more easily observe the cable.

The systems and method of the present disclosure provide many benefits by being able to use photogrammetry and/or lidar to determine position of the reflective cables of a geophysical survey system. Conventionally, strict geometries formed by cables used in a geophysical survey system are often used to determine position of the cable, which takes time to deploy and measure. As such, systems and method of the present users may be able to reduce the time it takes to deploy cables in the physical environment because positioning of the reflective cable is less important when the position of the reflective cable can be easily determined after deploying the reflective cable using photogrammetry or lidar. Also, measuring accurate elevation differences of the cable layout will constrain geophysical survey computer models more accurately.

Referring now to FIG. 1, an embodiment of a reflective cable locating system 100 is illustrated. In the illustrated embodiment, the reflective cable locating system 100 includes a cable locator device 102 provided in a physical environment 103. The physical environment 103 may be any indoor and/or outdoor space that may be contiguous or non-contiguous. For example, the physical environment may include a yard, a park, a stadium, a field, a mine site, a lake, an ocean, a cave, a mineshaft, and/or other spaces. The physical environment 103 may be defined by geofencing techniques that may include specific geographic coordinates such as latitude, longitude, and/or altitude, and/or operate within a range defined by a wireless communication signal. The physical environment 103 may include a geophysical survey system 104 (e.g., a resistivity geophysical survey system, an electromagnetic geophysical survey system, and/or any other geophysical survey system). The geophysical survey system 104 may include a reflective cable system that includes a reflective cable, as discussed below, that are included in a geophysical survey application and may need to be positioned or position(s) of the reflective cable of the geophysical survey system 104 may need to be determined for generating accurate geophysical survey computer models of a sub-ground of the physical environment 103. While the reflective cable locating system 100 is described as locating and determining position of reflective cables in geophysical survey applications, one skill in the art in possession of the present disclosure would recognize that the reflective cable locating systems and methods described herein may be used for other uses and objects such as, for example, cables in electrical grids and telecommunications, cables in construction, and/or locating and determining position of other objects in a physical environment besides cables using photogrammetry and/or lidar.

In various embodiments, the cable locator device 102 is described as mobile computing devices such as laptop/notebook computing devices, tablet computing devices, mobile phones, wearable computing devices, aircraft, drone devices including unmanned aerial vehicles (UAV), and/or other devices that can perform photogrammetry and/or lidar methods. However, in other embodiments, the cable locator device 102 may be provided by desktop computing devices, server computing devices, and/or a variety or combination of other computing devices that would be apparent to one of skill in the art in possession of the present disclosure. In yet other embodiments, the cable locator device 102 may simply include a light source (e.g., a headlamp, a headlight, a flashlight, etc.) that may be used by a user to reflect light off of reflective cables included in the geophysical survey system 104 such that the user may observe the reflected light and visualize the location of a reflective cable in the physical environment 103.

In various embodiments, the cable locator device 102 may perform methods of the present disclosure as a standalone device. However, in other embodiments, the cable locator device 102 may include communication units having one or more transceivers to enable the cable locator device 102 to communicate with the geophysical survey system 104 and/or other geophysical sensor devices, other cable locator devices, and/or a server device 106. Accordingly and as disclosed in further detail below, the cable locator device 102 may be in communication with the geophysical survey system 104 directly or indirectly. However, in other embodiments, the cable locator device 102 may not be in communication with the geophysical survey system 104. As used herein, the phrase "in communication," including variances thereof, encompasses direct communication and/or indirect communication through one or more intermediary components and does not require direct physical (e.g., wired and/or wireless) communication and/or constant communication, but rather additionally includes selective communication at periodic or aperiodic intervals, as well as one-time events.

For example, the cable locator device 102 and/or the geophysical survey system 104 in the reflective cable locating system 100 of FIG. 1 may include first (e.g., long-range) transceiver(s) to permit the cable locator device 102 and/or the geophysical survey system 104 to communicate with a network 108 via a communication channel 110a and a communication channel 110b, respectively. The network 108 may be implemented by an example mobile cellular network, such as a long term evolution (LTE) network or other third generation (3G), fourth generation (4G) wireless network, or fifth-generation (5G) wireless network. However, in some examples, the network 108 may be additionally or alternatively be implemented by one or more other communication networks, such as, but not limited to, a satellite communication network, a microwave radio network, and/or other communication networks.

The cable locator device 102 and/or the geophysical survey system 104 additionally may include second (e.g., short-range) transceiver(s) to permit the cable locator device 102 to communicate with the geophysical survey system 104 via a communication channel 112. In the illustrated example of FIG. 1, such second transceivers are implemented by a type of transceiver supporting short-range (i.e., operate at distances that are shorter than the long range transceivers) wireless networking. For example, such second transceivers may be implemented by Wi-Fi transceivers (e.g., via a Wi-Fi Direct protocol), Bluetooth® transceivers, infrared (IR) transceiver, and other transceivers that are configured to allow the cable locator device 102 and/or the geophysical survey system 104 to intercommunicate via an ad-hoc or other wireless network.

The reflective cable locating system 100 also includes or may be in connection with a server device 106. For example, the server device 106 may include one or more server devices, storage systems, cloud computing systems, and/or other computing devices (e.g., desktop computing device(s), laptop/notebook computing device(s), tablet computing device(s), mobile phone(s), etc.). As discussed below, the server device 106 may be used to use geophysical survey information gathered from the cable locator device 102 and/or the geophysical survey system 104 to generate geophysical survey computer models of the subsurface of the physical environment 103. However, one of skill in the art in possession of the present disclosure will recognize that some other "on-site" computing device, the cable locator device 102, and/or the geophysical survey system 104 may gather the geophysical survey information used and generate a geophysical survey computer model of the subsurface of the physical environment 103.

Figure 2:
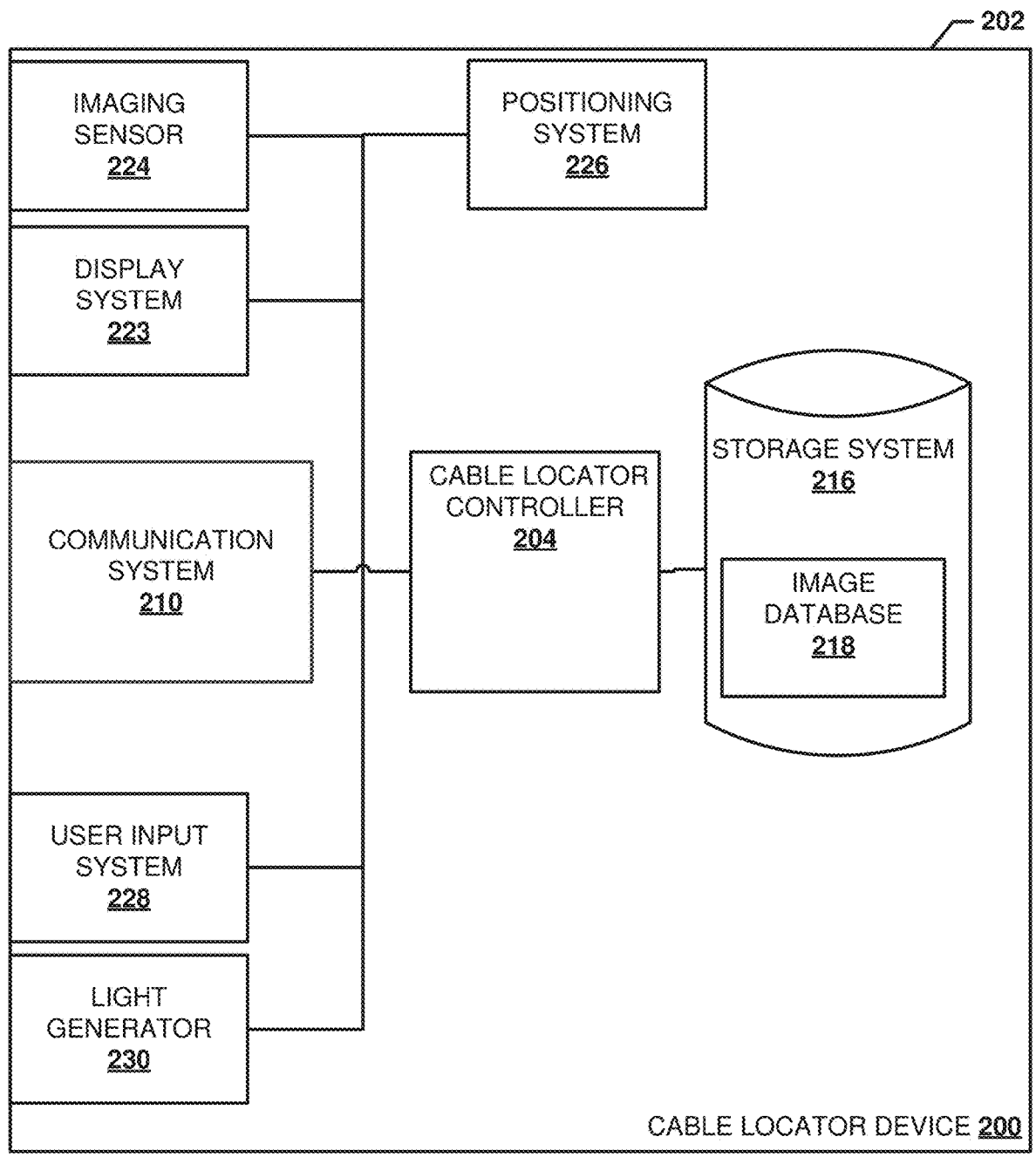
FIG. 2 is a schematic view illustrating an embodiment of a cable locator device used in the reflective cable locating system of FIG. 1.

Referring now to FIG. 2, an embodiment of a cable locator device 200 is illustrated that may be the cable locator device 102 discussed above with reference to FIG. 1, and which may be provided by a mobile computing device such as a laptop/notebook computing device, a tablet computing device, a mobile phone, an aircraft, a drone such as, for example, a UAV, and a wearable computing device. In the illustrated embodiment, the cable locator device 200 includes a chassis 202 that houses the components of the cable locator device 200. Several of these components are illustrated in FIG. 2. For example, the chassis 202 may house a processing system (not illustrated) and a non-transitory memory system (not illustrated) that includes instructions that, when executed by the processing system, cause the processing system to provide a cable locator controller 204 that is configured to perform the functions of the cable locator controller and/or the cable locator devices discussed below.

The chassis 202 may further house a communication system 210 that is coupled to cable locator controller 204 (e.g., via a coupling between the communication system 210 and the processing system). The communication system 210 may include software or instructions that are stored on a computer-readable medium and that allow the cable locator device 200 to send and receive information through the communication networks discussed above. For example, the communication system 210 may include a first communication interface to provide for communications through the communication network 108 as detailed above (e.g., first (e.g., long-range) transceiver(s)). In an embodiment, the first communication interface may be a wireless antenna that is configured to provide communications with IEEE 802.11 protocols (Wi-Fi), cellular communications, satellite communications, other microwave radio communications and/or communications. The communication system 210 may also include a second communication interface that is configured to provide direct communication with other user devices, geophysical survey systems, sensors, storage devices, and other devices within the physical environment 103 discussed above with respect to FIG. 1 (e.g., second (e.g., short-range) transceiver(s)). For example, the second communication interface may be configured to operate according to wireless protocols such as Bluetooth®, Bluetooth® Low Energy (BLE), near field communication (NFC), infrared data association (IrDA), ANT®, Zigbee®, Z-Wave® IEEE 802.11 protocols (Wi-Fi), and other wireless communication protocols that allow for direct communication between devices.

The chassis 202 may house a storage device (not illustrated) that provides a storage system 216 that is coupled to the cable locator controller 204 through the processing system. The storage system 216 may include an image database 218 that stores various images files captured by an imaging sensor 224 discussed below. In addition, the storage system 216 may include at least one application that provides instruction to the cable locator controller 204 when processing images to determine a location of a reflective cable, to determine a position of the reflective cable, and/or to generate geophysical survey models.

The chassis 202 may also house an imaging sensor 224 (e.g., a two-dimensional image capturing camera, a three-dimensional image capturing camera, an infrared image capturing camera, an ultra violet image capturing camera, a depth capturing camera, similar video recorders, and/or a variety of other image or data capturing devices) that is coupled to the cable locator controller 204 through the processing system. The imaging sensor 224 may be a camera, a photodetector, and/or any other photo sensor device that may be used to gather visual information from the physical environment 103 surrounding the cable locator device 200 for locating a reflective cable within the physical environment 103.

The chassis 202 may also house a light generator 230 that is coupled to the cable locator controller 204 through the processing system. The light generator 230 may include, for example, a laser device (e.g., a laser used in lidar), a flash device (e.g., a flash LED, an electronic flash, etc.), and/or any other light generator for use in lidar and/or photogrammetry applications that would be apparent to one of skill in the art in possession of the present disclosure.

The chassis 202 may also include a positioning system 226 that is coupled to the cable locator controller 204 through the processing system. The positioning system 226 may include sensors for determining the location and position of the cable locator device 200 in the physical environment 103. For example the positioning system 226 may include a global positioning system (GPS) receiver, a real-time kinematic (RTK) GPS receiver, a differential GPS receiver, a Wi-Fi based positioning system (WPS) receiver, an accelerometer, a gyroscope, a compass, and/or any other sensor for detecting and/or calculating the orientation and/or movement of the cable locator device 200, and/or other positioning systems and components.

In various embodiments, the chassis 202 also houses a user input subsystem 228 that is coupled to the cable locator controller 204 (e.g., via a coupling between the processing system and the user input subsystem 228). In an embodiment, the user input subsystem 228 may be provided by a keyboard input subsystem, a mouse input subsystem, a track pad input subsystem, a touch input display subsystem, and/or any other input subsystem. The chassis 202 also houses a display system 223 that is coupled to the cable locator controller 204 (e.g., via a coupling between the processing system and the display system 223). In an embodiment, the display system 223 may be provided by a display device that is integrated into the cable locator device 200 and that includes a display screen (e.g., a display screen on a laptop/notebook computing device, a tablet computing device, a mobile phone, or wearable device), or by a display device that is coupled directly to the cable locator device 200 (e.g., a display device coupled to a desktop computing device by a cabled or wireless connection). While a specific embodiment of the cable locator device 200 is illustrated, one of skill in the art in possession of the present disclosure would recognize that other components would fall within the scope of the present disclosure. For example, the cable locator device 200 may include components required for the cable locator device 200 to fly such as required for an UAV and/or include a variety mirrors and other components for lidar applications while still remaining within the scope of the present disclosure.

Figure 3:
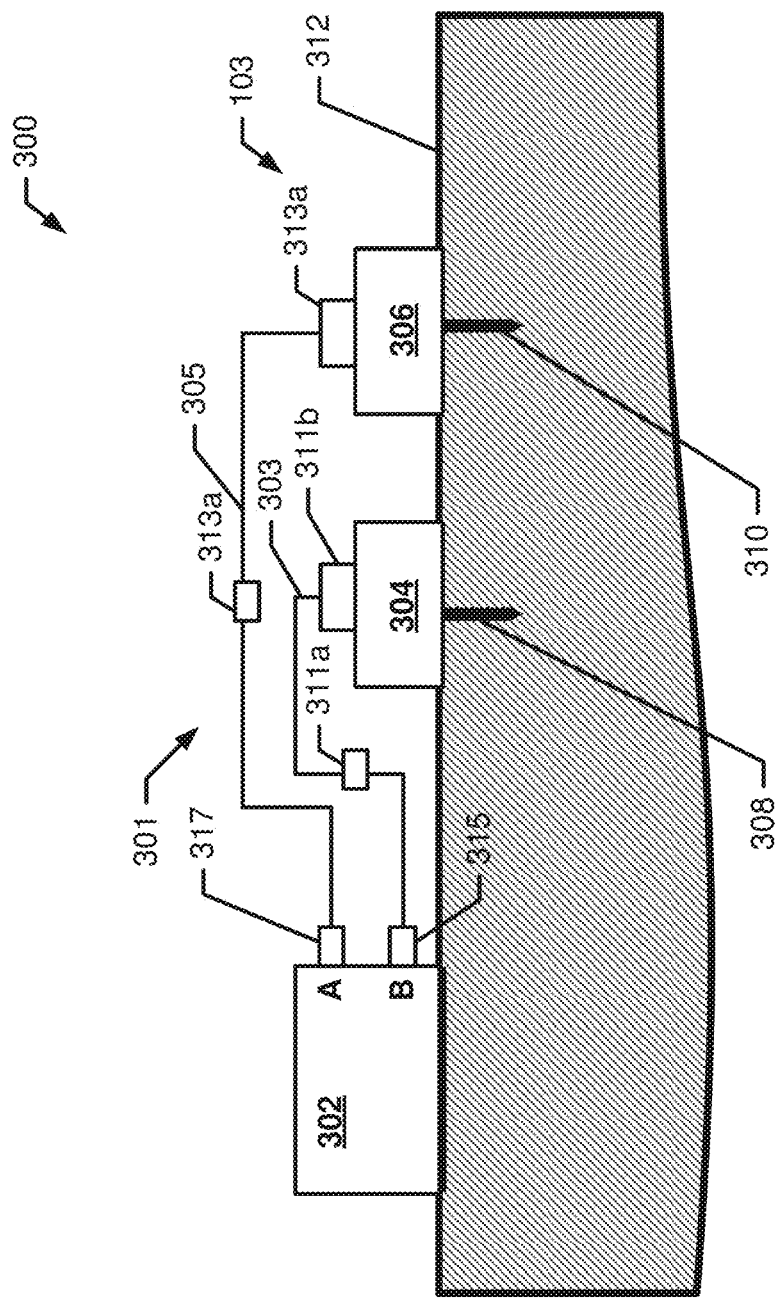
FIG. 3 is a schematic view illustrating an embodiment of a geophysical survey system used in the reflective cable locating system of FIG. 1.

Referring now to FIG. 3, an embodiment of a geophysical survey system 300 is illustrated that may be the geophysical survey system 104 discussed above with reference to FIG. 1. While a geophysical survey system 300 is illustrated that is used for resistivity methods and models, one of skill in the art in possession of the present disclosure will recognize that the reflective cable system and/or reflective components/objects herein may benefit other geophysical surveys and geophysical modelling such as, for example, electromagnetic methods and systems. Thus, the geophysical survey system 300 is merely an example of one type of geophysical survey system 104 and other geophysical survey systems that incorporate cables and devices where knowledge of the location of those devices and cables are helpful in generating geophysical survey models is contemplated.

The geophysical survey system 300 may include a reflective cable system 301, a geophysical survey controller 302, and at least two survey probes 304 and 306. In the example of FIG. 3, survey probe 306 is connected to an output "A" of the geophysical survey controller 302 by a reflective cable 305 of the reflective cable system 301, and survey probe 304 is connected to an output "B" of the survey controller 302 by a reflective cable 303 of the reflective cable system 301. In some cases or embodiments, the reflective cables 303 and/or 305 may be provided by an integrated multiconductor cable that includes a plurality of take-outs. For example, the reflective cable 303 may include take-outs 311a and up to 311b and the reflective cable 305 may include take-outs 313a and up to 313b. The take-outs 311a, 311b, 313a, and 313b may electrically and, in some embodiments, mechanically couple with survey probes such as for example survey probes 304 and 306. The reflective cable system 301 may also include one or more connectors 315 and/or 317. For example, the reflective cable 303 may be coupled to a connector 315 and the reflective cable 305 may be coupled a connector 317. The connectors 315 and the connector 317 may be configured to electrically and, in some embodiments, mechanically couple the reflective cables 303 and 305, respectively, to the geophysical survey controller 302. The simplified illustration of the geophysical survey system 300 of FIG. 3 is merely illustrative and should not be taken as limiting.

Additionally, the survey probe 304 includes an electrode 308, and the survey probe 306 includes an electrode 310. In some cases or embodiments, larger numbers of probes, more complex topologies, and different forms of connection (e.g., buried probes, borehole positioned probes, towed aquatic arrays, etc.) may be employed. Referring illustratively and without limitation, to FIG. 3, each of the illustrated electrodes 308/310 is inserted into the ground 312 of the physical environment 103 to allow for measurement of an electrical property (e.g., apparent resistivity, resistance, induced polarization, self-potential, etc.) of the ground 312. In one example, an electrical stimulus (e.g., an injection current) may be provided by the geophysical survey controller 302 and transmitted through one of the reflective cables 303/305 to one of the survey probes 304/306, and thus to one of the electrodes 308/310, whereby the other one of the electrodes 308/310 serves as a return path for the electrical stimulus.

While examples of embodiments of the geophysical survey system 300 are shown and discussed herein with application to terrestrial measurements, one of skill in the art will recognize that other measurement application environments (e.g., marine environments), as well as other components of the geophysical survey system 300 which have been omitted for clarity of discussion, may be included in the geophysical survey system 300 and will fall within the scope of the present disclosure. For example, while two survey probes 304, 306 are shown, the geophysical survey system 300 may include a sizable array of survey probes configured in a variety of array types including Schlumberger, Wenner alpha, Wenner beta, Wenner gamma, pole-pole, dipole-dipole, pole-dipole, equatorial dipole-dipole, or any combination thereof. Moreover, any of the survey probes included in such an array may be configured according to a particular operational mode such as a current injection configuration, a current return configuration, or a voltage sense configuration.

Referring now to FIG. 4, an embodiment of a reflective cable 400 is illustrated that may be the reflective cables 303/305 discussed above with reference to FIG. 3. The reflective cable 400 may include a conductive wire 402 surrounded by an electrically insulating sheath 404 that provides an exterior surface 406. The electrically insulating sheath 404 may include a non-reflective sheath portion 404a and a reflective sheath portion 404b. The reflective sheath portion 404b may be located opposite the non-reflective sheath portion 404a from the conductive wire 402 and be included on the exterior surface 406. The reflective sheath portion 404b may include a reflective material that reflects visible light and/or other electromagnetic waves (e.g., infrared, ultra violet, etc.) provided by a light source back to the light source. For example, the reflective material may be material that reflects the spectrum of light that was provided from the light source back to the light source without absorbing that spectrum. The reflective sheath portion 404b may include reflective material such as a plurality of microprisms (e.g., orthogonal 3-planar prisms), glass beads, microspheres and/or any other reflective materials that would be apparent to one of skill in the art in possession of the present disclosure that are embedded in the electrically insulating sheath 404 and exposed on the exterior surface 406 of the electrically insulating sheath 404, and/or disposed on the exterior surface 406 of the electrically insulating sheath 404. Thus, in various embodiments, the reflective sheath portion 404b may include a portion of the electrically insulating sheath 404 that is wrapped in reflective tape and/or coated in a reflective paint. The reflective material in the reflective sheath portion 404b may be configured to reflect light provided by a light source back to the light source. In various embodiments, the reflective material may be selected such that a maximum amount of backscattered light is directed 180 degrees back to the light source.

Figure 6:
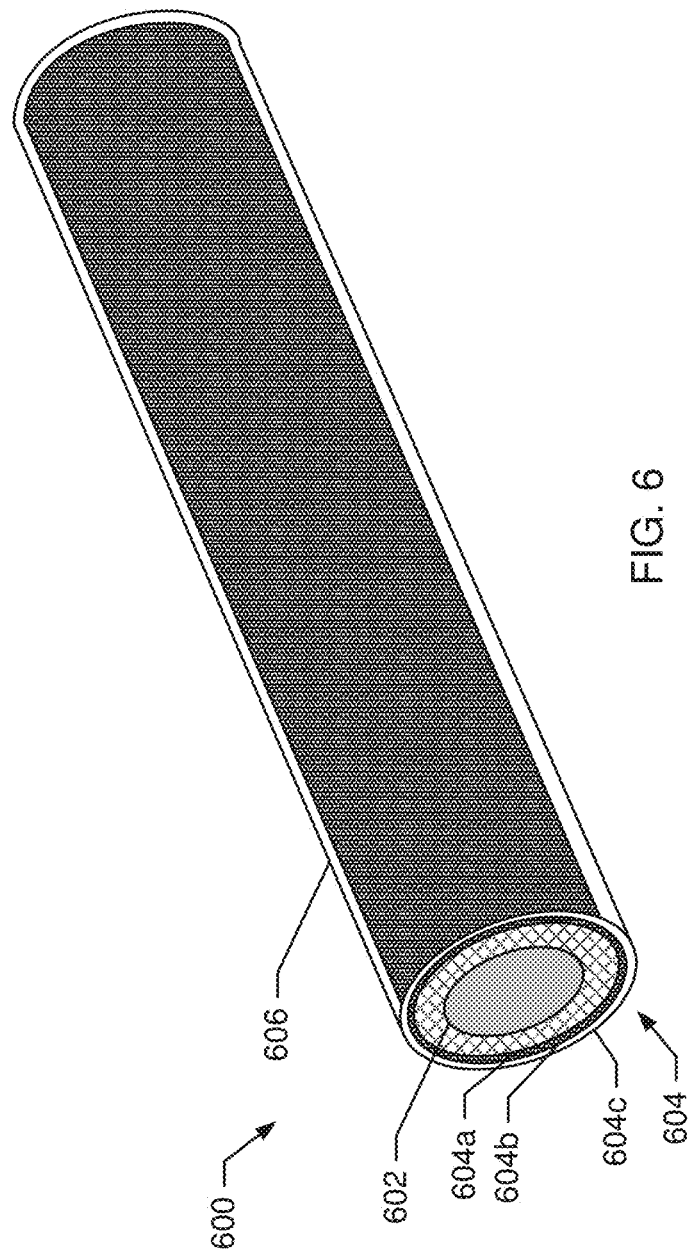
FIG. 6 is a perspective view illustrating an embodiment of a reflective cable of the geophysical survey system of FIG. 3.

Referring now to FIG. 5, an embodiment of a reflective cable 500 is illustrated that may be the reflective cables 303/305 discussed above with reference to FIG. 3. The reflective cable 500 may include a conductive wire 502 surrounded by an electrically insulating sheath 504 that provides an exterior surface 506. The electrically insulating sheath 504 may include the reflective material, discussed above in FIG. 4, throughout the thickness of the electrically insulating sheath 504. In yet other embodiments and referring to FIG. 6, a reflective cable 600, that may be the reflective cable 303 and/or 305 discussed above with reference to FIG. 3, may include a conductive wire 602 surrounded by an electrically insulating sheath 604 that provides an exterior surface 606 of the reflective cable 600. The electrically insulating sheath 604 many include a non-reflective sheath portion 604a, a reflective sheath portion 604b, and a transparent sheath portion 604c. The reflective sheath portion 604b may be located opposite the non-reflective sheath portion 604a from the conductive wire 602. The transparent sheath portion 604c may be located opposite the reflective sheath portion 604b from the non-reflective sheath portion 604a and provide the exterior surface 606 of the reflective cable 600. The transparent sheath portion 604c may be clear such that light may pass through the transparent sheath portion 604c to the reflective sheath portion 604b from a light source and reflected light may pass through the transparent sheath portion 604c from the reflective sheath portion 604b to the light source. While the reflective sheath portions 404b and 604b and the electrically insulating sheath 504 that includes reflective material throughout its thickness are illustrated as being contiguous, one of skill in the art in possession of the present disclosure will recognize that the reflective sheath portions 404b and 604b and the electrically insulating sheath 504 may be non-contiguous in that the reflective sheath portions 404b and 604b and the electrically insulating sheath 504 need not to surround the non-reflective sheath portion 404a around the entire circumference of the cable and/or length of the cable. For example, the reflective sheath portions 404b and 604b may spiral along the length of the reflective cables 400 and 600, respectively. In other examples, the reflective sheath portion 404b and 604b may include spaced apart rings around their respective reflective cable 400 and 600 such that each reflective ring is spaced apart by electrically insulating portions that provide no reflective material. Similarly, the electrically insulating sheath 504 that is reflective may form spirals, rings, and/or other shapes that are separated by the portions of the electrically insulating sheath that do not include reflective material.

Figure 7:
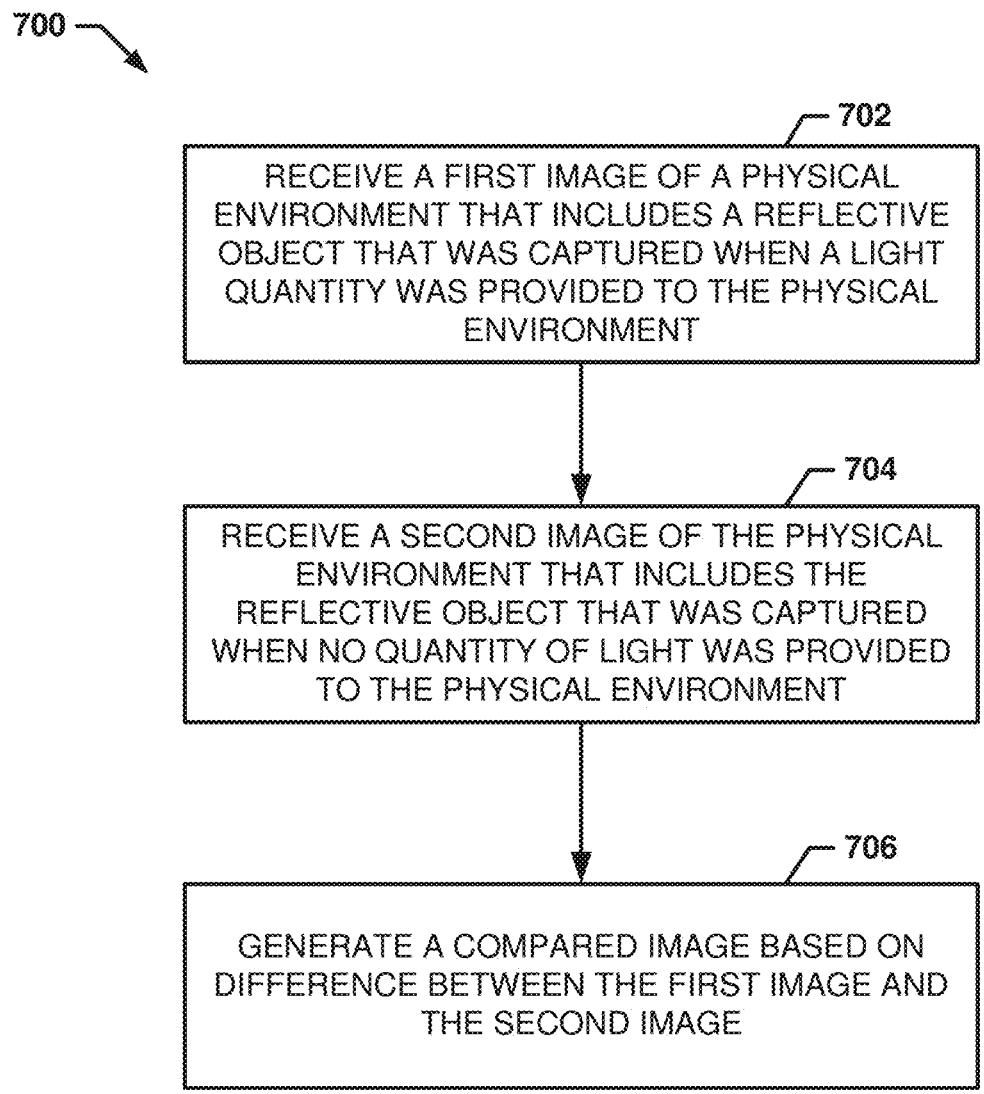
FIG. 7 is a flow chart illustrating an embodiment of a method of locating a reflective cable in a physical environment.

Referring now to FIG. 7, an embodiment of a method 700 of locating a reflective cable is illustrated. The method 700 will be discussed in reference to the FIGS. 1, 2, and 3 above. The method 700 begins at block 702 where a first image of a physical environment that includes a reflective cable is received. In an embodiment of block 702, the cable locator controller 204 of the cable locator device 102 may receive a first image of the physical environment 103 that includes a reflective cable (e.g., reflective cable 303 and/or 305) of the geophysical survey system 104 that is captured by the imaging sensor 224. For example, the imaging sensor 224 may include a camera that captures a photograph of the physical environment 103 that includes the reflective cables 303 and/or 305 of the reflective cable system 301. The first image may be stored in the image database 218 of the storage system 216 after being captured by the imaging sensor 224 and/or after the first image is provided to the cable locator controller 204.

In various embodiments, the imaging sensor 224 may capture the first image for the physical environment 103 when a light generator 230 is used during the capture of the first image to illuminate the physical environment 103, which may enhance the first image. The light generator 230 may generate a first quantity of light. For example, the light generator 230 may generate 100-1,000,000 lumens of light, such as full spectrum of visible light. However, one of skilled in the art in possession of the present disclosures will recognize that other quantities of light and/or spectrums of light may be contemplated and fall within the scope of the present disclosure.

In various embodiments, the imaging sensor 224 may be at a first position and a first orientation when the image is captured by the imaging sensor 224. As discussed above, the cable locator device 102 may include the positioning system 226 that may be used to determine position information of the cable locator device 102 such as, for example, longitude, latitude, altitude, and/or any other position information. As discussed above the positioning system 226 may include a global positioning system (GPS) receiver, a real-time kinematic (RTK) GPS receiver, a differential GPS receiver, a Wi-Fi based positioning system (WPS) receiver, and/or other positioning systems and components. In various embodiments, the positioning system 226 may operate in conjunction with a field device coupled to the cable locator device 102 via the communication systems 210. The field device may provide components of the global positioning system (GPS) receiver, the real-time kinematic (RTK) GPS receiver, the differential GPS receiver, the Wi-Fi based positioning system (WPS) receiver. For example, the field device may include a reference station of a fixed, known position for RTK GPS and/or differential GPS.

As discussed above, the positioning system 226 that may also be used to determine orientation information of the cable locator device 102 and/or the imaging sensor 224 such as orientation of the cable locator device 102 in three-dimensional space. As discussed above, the positioning system 226 may include an accelerometer, a gyroscope, an altimeter, a compass, and/or any other sensor for detecting and/or calculating the orientation and/or movement of the cable locator device 102 and/or the imaging sensor 224. The positioning system 226 may provide orientation information to the cable locator controller 204 such as the distance the cable locator device 102 is from the ground of the physical environment 103, an angle that cable locator device 102 is in relation to the ground of the physical environment 103, a direction at which the cable locator device 102 is facing in relation to a magnetic field of the physical environment 103, and/or a direction the cable locator device 102 is positioned in relation to gravity.

Figure 8A:
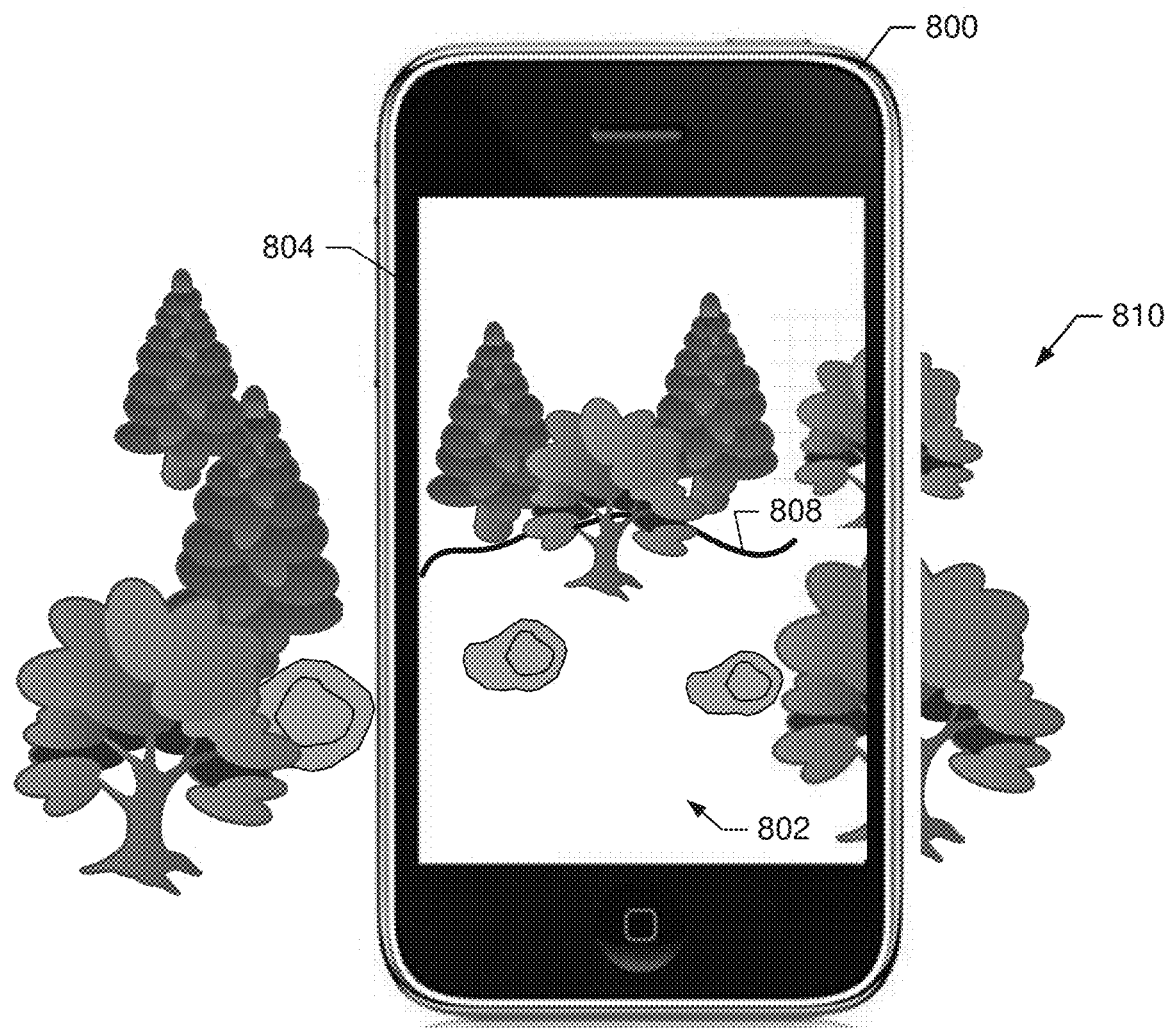
FIG. 8A is a screenshot of an embodiment of a cable locator device displaying an image of a physical environment that includes a reflective cable during the method of FIG. 7.

In an embodiment and with reference to FIG. 8A, the cable locator controller 204 may provide the first image to the display system 223 for display on a display screen. For example, a screenshot of a specific example of the method 700 for locating a reflective cable in a physical environment is illustrated in FIG. 8A. FIG. 8A illustrates a cable locator device 800, which may be any of the cable locator devices 102/200 described above. The cable locator controller 204 via the display system 223 of the cable locator device 800 may render a first image 802 which may be the first image discussed above in reference to block 702 of method 700 on a display screen 804 of the cable locator device 800. The first image 802 may include a reflective cable 808, which may be one of the reflective cables 303 or 305 of the geophysical survey system 104. The reflective cable 808 may be positioned in the physical environment 810, which may be the physical environment 103, discussed above, and include vegetation, rocks, obstacles, structures, and/or any other objects that may obscure and/or camouflage the reflective cable 808. The objects within the environment may make it difficult for a user, such as a user performing a geophysical survey, to locate the reflective cable 808 with the user's eyes.

Alternatively or in addition to objects obscuring the reflective cable 808 with the physical environment 810, the physical environment 810 may include an ambient illuminance that may make locating the reflective cable 808 difficult for a user using sight alone. For example, the physical environment 810 may be at night, dusk, dawn, in a cave, in an underground mine, underwater, in a dark building and/or include other low ambient lighting conditions that would be apparent to one of skill in the art in possession of the present disclosure. Such physical environments 810 with low ambient lighting conditions may provide an ambient illuminance of 0-50 lux; however in other examples the physical environment 810 may provide an ambient illuminance of 0-10 lux. If the physical environment 810 includes the low ambient illuminance, the reflective cable 808, if not completely blocked by objects, may illuminate when a user shines a light at the reflective cable 808. As such the reflective cable 808 may be easily detectable with a flashlight or headlamp such that the reflective cable 808 is visually distinguishable by the human eye when a light source is added to the physical environment 810 when compared to when the light source is taken away. In another example, when capturing the first image 802 with the imaging sensor 224 and using the light generator 230 of the cable locator device 102 during the in the low ambient illuminance conditions, the light reflected by the reflective cable 808 should allow the user to easily locate the reflective cable 808 in the first image 802 as it should reflect back more light from the light generator 230 than other objects in the environment making the reflective cable visually distinguishable from the other objects in the physical environment 810.

However, in some physical environments with high ambient illuminance, the differences between a reflective cable 808 with a light source introduced to the physical environment 810 and how the user perceives the physical environment 810 without the light source may be visually negligible such that a human eye cannot tell the difference between the two situations. Similarly, differences between the reflective cable 808 in the first image 802 that was captured using a quantity of light generated by the light generator 230 and how the user perceives the physical environment 810 without the quantity of light from the light generator 230 or an image that does not include light generated by the light generator 230 may be visually negligible such that a human eye cannot tell the difference between the two situations. For example, the physical environment 810 may be during the day, during peak sunlight, during a cloudy day, in a well-lit enclosure, and/or include other high ambient lighting conditions that would be apparent to one of skill in the art in possession of the present disclosure. Such physical environments 810 with high ambient lighting conditions may provide an ambient illuminance of 50-100,000 lux; however in other examples the physical environment 810 may provide an ambient illuminance of over 10 lux. If the physical environment 810 includes the high ambient illuminance, the reflective cable 808, especially if partially obscured by objects, may be difficult to locate by a user and may not provide the reflective benefits of the reflective cable as experienced in low ambient illuminance conditions as the reflectiveness is more difficult for a human eye to perceive in high ambient illuminance conditions.

As such, the method 700 may proceed to block 704 where a second image of the physical environment that includes the reflective cable is received. In an embodiment of block 704, the cable locator controller 204 of the cable locator device 102 may receive a second image of the physical environment 103 that includes the geophysical survey system 104 that is captured by the imaging sensor 224. For example, the camera of the imaging sensor 224 may capture a second photograph of the physical environment 103 that includes the reflective cable 303 and/or 305 of the reflective cable system 301. The imaging sensor 224 may capture the image for the physical environment 103 when a light generator 230 is used during the capture of the second image to illuminate the physical environment 103, which may enhance the second image. The light generator 230 may generate a second quantity of light that is less than the first quantity of light that was used during block 702. However, in other embodiments, the light generator 230 may be disabled during the capture of the second image by the imaging sensor 224 such that no light is provided to the physical environment 103 by the light generator 230. The first quantity of light and the second quantity of light may be selected such that the cable locator controller 204 can distinguish the reflective cable 303 and/or 305 in the first image from the reflective cable 303 and/or 305 in the second image. As discussed above, the differences between the reflective cable 303 and/or 305 in the first image and the reflective cable 303 and/or 305 in the second image may be visually negligible by a user's eye in high ambient illuminance conditions and thus may require the use of the cable locator controller 204 to distinguish the differences.

In various embodiments, the imaging sensor 224 may be at the first position and the first orientation when the second image is captured by the imaging sensor 224. The second image may be captured prior to or subsequent to the first image such that the first image and second image are captured in short succession to minimize the change in position and orientation between the two images, which allows for a more accurate comparison of the first and second images in block 706 of method 700, discussed below. However, in other embodiments the second image may be captured at a second position and/or a second orientation that is different than the first position and/or the first orientation, respectively.

Figure 8B:
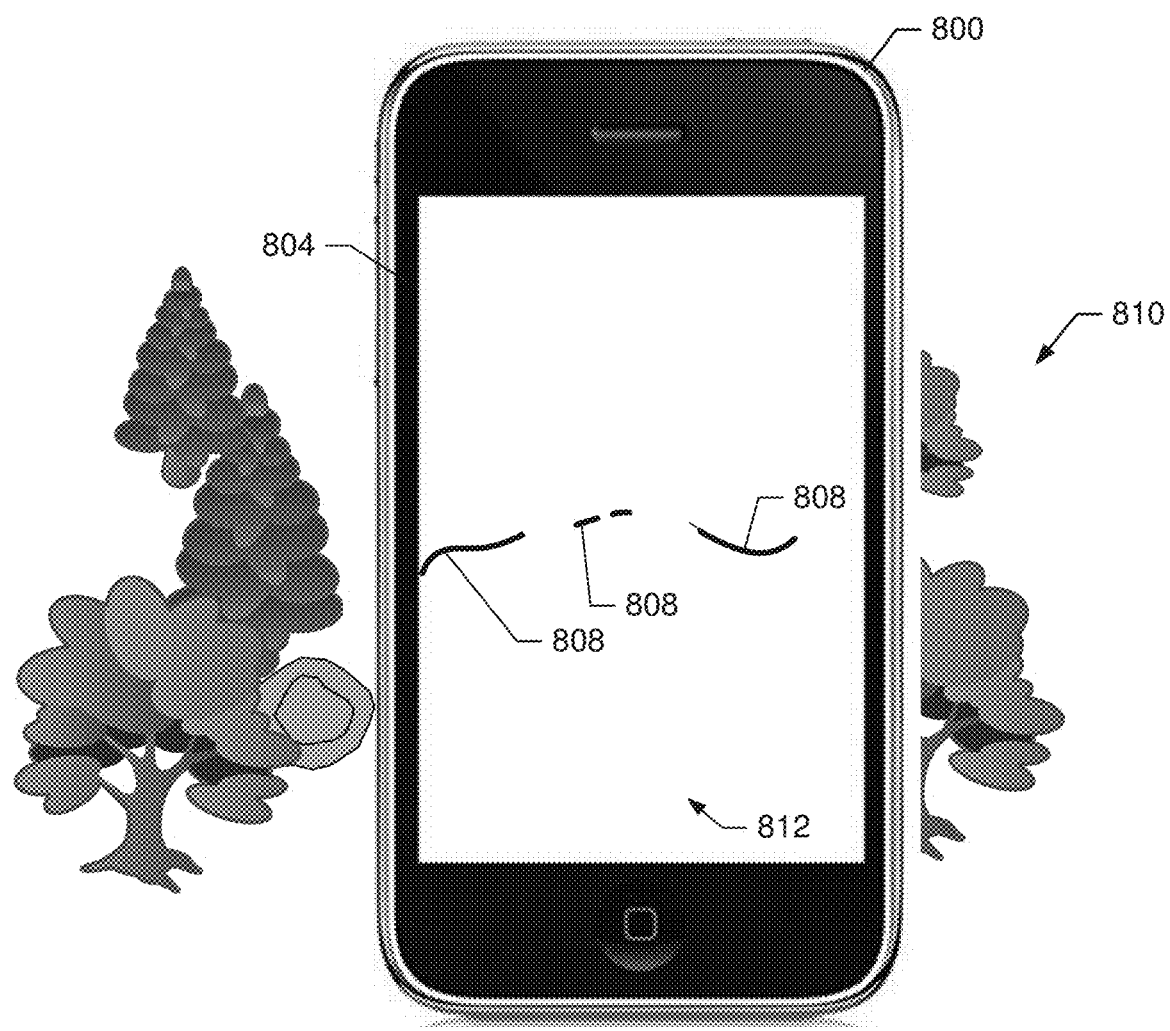
FIG. 8B is a screenshot of an embodiment of the cable locator device displaying a compared image of the reflective cable during the method of FIG. 7.

The method 700 then proceeds to block 706 where the first image is compared to the second image to generate a compared image. In an embodiment of block 706, the cable locator controller 204 may compare and determine the differences between the first image and the second image and generate a compared image of the physical environment 103 that includes the reflective cable 303 and/or 305. The compared image may illustrate differences between the first image and the second image such as a difference in illuminance of the reflective cable 303 and/or 305 that distinguishes the reflective cable 303 and/or 305 from other objects in the physical environment 103. For example, and with reference to FIG. 8B, the cable locator device 800 may display a compared image 812 on the display screen 804 of the cable locator device 800. In the illustrated example, the compared image 812 may be generated by subtracting the differences between the first image and the second image. In a specific example, the first image and the second image may be converted to respective Tagged Image File Format (TIFF) files and the respective TIFF files may be subtracted from each other. Because the reflective cable 808 will reflect more light generated by the light generator 230 back to the imaging sensor 224 than other objects in the physical environment 810, there will be a greater difference between the illuminance of the reflective cable 808 in the first image 802 and the illuminance of the reflective cable 808 a second image when less light is generated by the light generator 230 or when no light is generated by the light generator 230. As illustrated in the compared image 812, the portions of the reflective cable 808 that are in view of the imaging sensor 224 are displayed in the compared image 812, while the other objects in the physical environment 810 are removed due to no or minimal difference in illuminance between the other objects in the physical environment 810 in the first image 802 and a second image. While the method 700 is described as providing benefits in physical environments with high ambient illuminance conditions, the method 700 may provide similar benefits in low ambient illuminance conditions discussed above. For example, there may be many objects or cables in the physical environment 103 that are reflective, thus making it difficult for a user to distinguish the objects at night when shining a light in the physical environment 103.

Figure 9:
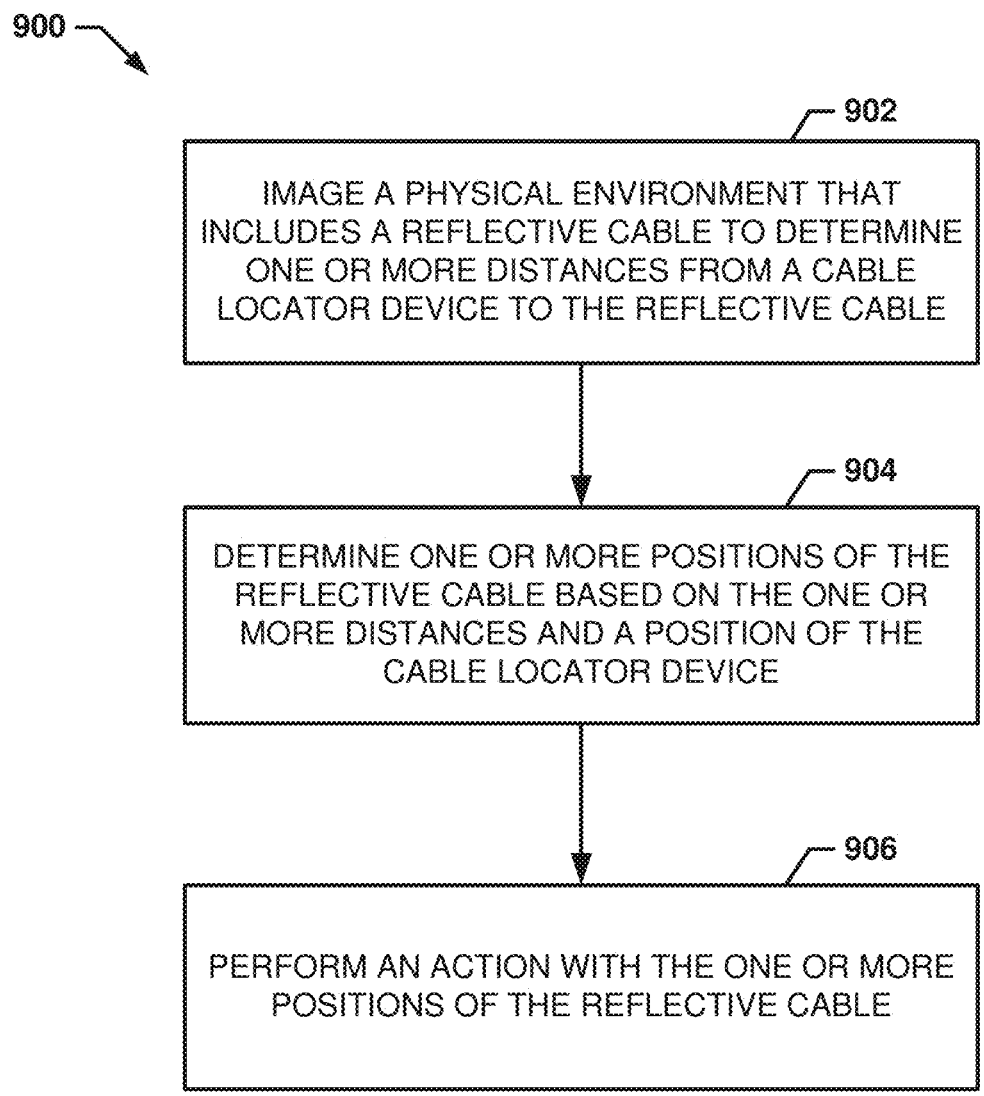
FIG. 9 is a flow chart illustrating an embodiment of a method of determining a position of a reflective cable in a physical environment.

Referring now to FIG. 9, a method 900 of determining a position of a reflective cable is illustrated. The method 900 will be discussed in reference to the FIGS. 1, 2, and 3 above. The method 900 begins at block 902 where a physical environment that includes a reflective cable is imaged. In an embodiment of block 902, the cable locator device 102 may image the physical environment 103 that includes the reflective cable 303 and/or 305. The imaging of the physical environment 103 may include an imaging technique from which a distance between the cable locator device 102 and the objects in the image may be determined. For example, the cable locator device 102 may be configured to perform imaging such as photogrammetry. As such, the imaging sensor 224 may include a camera that captures at least two photographs of the physical environment 103 such that each photograph is captured while the cable locator device 102 is a two different positions and/or orientations. The cable locator controller 204 and/or a photogrammetry engine provided on the server device 106 that receives the photographs over the network 108 from the cable locator device 102 may reconstruct the photographs such that a three-dimensional model of the physical environment 103 is generated from which a distance from an object, such as the reflective cable 303 and/or 305, in the physical environment 103 may be calculated from a position and an orientation of the camera when a photograph was captured that includes the object. In various embodiments, the photographs may be taken when light is provided by the light generator 230 such as a camera flash or strobe light to enhance the photographs.

In another example, the cable locator device 102 may be configured to perform imaging such as lidar. As such, the imaging sensor 224 may include a photodetector that captures backscattering of laser light provided by a laser that is provided by the light generator 230. The backscattering of laser light may occur when that laser light reaches an object in the physical environment 103. The cable locator controller 204 may calculate a time that the laser light takes to traverse the distance between the laser and the object and back to the photodetector from which the distance may be calculated between the object and the cable locator device 102 based on a known speed of light through air. These distances may be used in conjunction with the orientation and position of the cable locator device 102 to reconstruct a three-dimensional model of the physical environment 103 by the cable locator controller 204 and/or a lidar engine provided by the server device 106. While imaging techniques that use visible light are discussed herein, one of skill in the art that other electromagnetic radiation may be used to determine distance from the reflective cables 303 and/or 305 to the cable locator device 102. For example, photogrammetry may be performed using infrared photographs, ultraviolet induced visible fluorescence photographs, and/or any other electromagnetic radiation photographs that would be apparent to one of skill in the art in possession of the present disclosure.

In various embodiments, lidar and photogrammetry may not be sensitive enough to accurately reconstruct a cable in an image due to the amount reflected light received by the imaging sensor 224. This is especially true when a distance between the cable locator device 102 and the cable(s) of a geophysical survey system are relatively far away. By increasing the amount of reflected light received from the cable, reconstruction of the physical environment using lidar and photogrammetry may result in a more enhanced reconstruction of the cable in the image. The reflective cable 303 and/or 305 of the geophysical survey system 300 may provide more backscatter from the laser light provided by the light generator 230 used in lidar and more reflected light from a flash or strobe light provided by the light generator 230 used in photogrammetry. Thus, when reconstructing the physical environment 103 using lidar or photogrammetry, reflective cable 303 and/or 305 may be more enhanced than a cable without a reflective sheath portion.

The method 900 then proceeds to block 904 where one or more positions of the reflective cable are determined based on the one or more distances and a position of the cable locator device. In various embodiments, the cable locator controller 204 may determine one or more positions of the reflective cable 303 and/or 305 in the physical environment 103. Because the reflective cable 303 and/or 305 may span tens to hundreds of feet, the cable locator controller 204 may determine a plurality of positions of the reflective cable 303 and/or 305. Each position may be calculated using the distance between a point on the image of the reflective cable 303 and/or 305 and the image sensor 224 when the image was captured, a position of the image sensor 224 when the image was captured, and an orientation of the image sensor 224 when the image was captured. For example, the imaging sensor 224 may be at a first position and a first orientation when the image is captured by the imaging sensor 224. From the first position and the first orientation, as well as the distance between the imaging sensor 224 and a point on the reflective cable 303 and/or 305, the cable locator controller 204 may determine a position of the point on the reflective cable 303 and/or 305, such as a coordinate that includes longitude, latitude, and/or altitude, position that is relative to another object in the physical environment, and/or other position information that is useful to geophysical survey modeling.

As discussed above, the cable locator device 102 may include a positioning system 226 that may be used to determine position information of the cable locator device 102 such as, for example, longitude, latitude, altitude, and/or any other position information. As discussed above, the positioning system 226 that may be used to determine orientation information of the cable locator device 102 and the imaging sensor 224 such as orientation of the cable locator device 102 in three-dimensional space. For example, the positioning system 226 may include an accelerometer, a gyroscope, an altimeter, a compass, and/or any other sensor for detecting and/or calculating the orientation and/or movement of the cable locator device 102 and/or the imaging sensor 224. The positioning system 226 may provide orientation information to the cable locator controller 204 such as the distance the cable locator device 102 is from the ground of the physical environment 103, an angle that cable locator device 102 is in relation to the ground of the physical environment 103, a direction at which the cable locator device 102 is facing in relation to a magnetic field of the physical environment 103, and/or a direction the cable locator device 102 is positioned in relation to gravity.

The method 900 then proceeds to block 906 where an action is performed with the one or more positions of the reflective cable. In an embodiment of block 906, the cable locator controller 204 may perform a number of actions with the one or more positions of the reflective cable 303 and/or 305. In various embodiments, the cable locator controller 204 may output the one or more positions of the reflective cable on a display device provided by the display system 223. In various embodiments, the cable locator controller 204 may store the positions of the reflective cable 303 and/or 305 in the storage system 216 such that they may be retrieved at a later time. In various embodiments, the cable locator controller 204 may provide the one or more positions of the reflective cable 303 and/or 305 to the server device 106 via the communication system 210 and through the network 108. The server device 106 may use the one or more position of the reflective cable 303 and/or 305 in a geophysical survey of the sub-ground of the physical environment when the cables are being used in the geophysical survey such that more accurate geophysical survey models may be generated using reflective cable positions. However, in other embodiments, the cable locator controller 204 may provide the reflective cable positions to a geophysical surveying engine provided by instructions that are executed on the processing system of the cable locator device 200 and that is configured to generate geophysical survey models of the sub-ground of the physical environment 103 using the one or more positions of the reflective cables 303 and/or 305. While specific actions are illustrated, one of skill in the art in possession of the present disclosure would recognize that the position of the cable may be used for other actions as well.

Thus, systems and methods have been provided for locating and/or determining a position of a reflective cable of a geophysical survey system in a physical environment. The reflective cable may include a reflective sheath portion that includes reflective material such as microprisms and/or glass microspheres that are configured to reflect light back to a light source. As such, the reflective material may allow a user of a reflective cable system such as a geophysical survey system to locate reflective cables in physical environments that have low ambient illuminance using a light source such as a flashlight or head lamp to visually distinguish the reflective cable from other objects in the physical environment when the light from the light sources is directed at the reflective cable. Systems and methods have been provided that allow the user to locate the reflective cable in physical environments that have high ambient illuminance such that using a light source in the physical environment will result in a visually negligible difference in appearance of the reflective cable to the human eye compared to when viewing the reflective cable without the light source. Photographs of the physical environment that were taken with a flash and that were taken without a flash may be compared by a cable locator device to determine the differences between the photographs, which result in the reflective cable being distinguishable from the rest of the physical environment. The reflective cable also enhances accuracy of determining a position of the reflective cable using lidar or photogrammetry by directing more light to an image sensor provided by the cable locator device.

Figure 10:
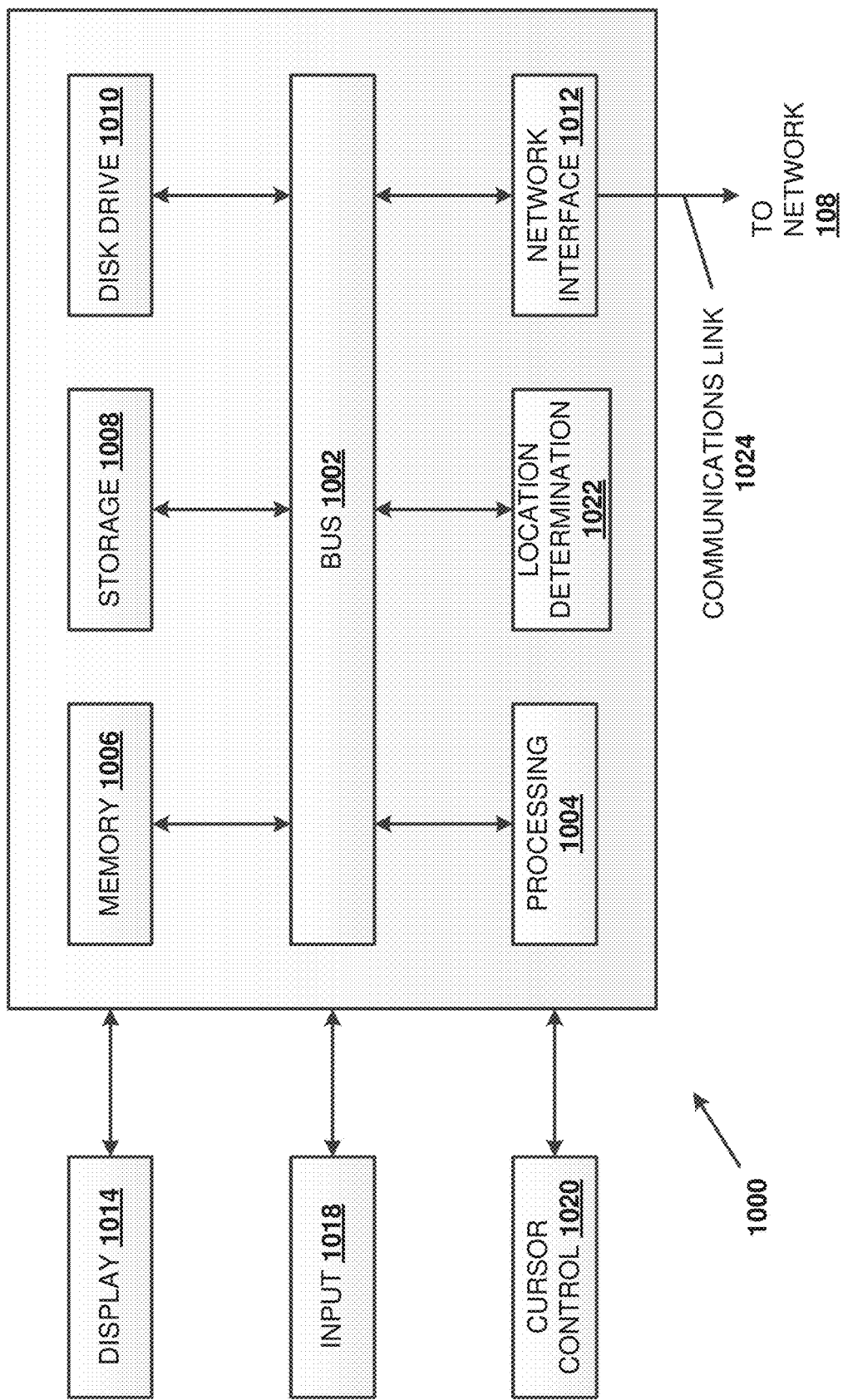
FIG. 10 is a schematic view illustrating an embodiment of a computer system.

Referring now to FIG. 10, an embodiment of a computer system 1000 suitable for implementing, for example, the cable locator device 102, 200, and 800, the geophysical survey systems 104 and 300, the server device 106 is illustrated. It should be appreciated that other devices utilized in the reflective cable locating system 100 discussed above may be implemented as the computer system 1000 in a manner as follows.

In accordance with various embodiments of the present disclosure, computer system 1000, such as a computer and/or a network server, includes a bus 1002 or other communication mechanism for communicating information, which interconnects subsystems and components, such as a processing component 1004 (e.g., processor, micro-controller, digital signal processor (DSP), etc.), a system memory component 1006 (e.g., RAM), a static storage component 1008 (e.g., ROM), a disk drive component 1010 (e.g., magnetic or optical), a network interface component 1012 (e.g., modem or Ethernet card), a display component 1014 (e.g., CRT, LCD, OLED), an input component 1018 (e.g., keyboard, keypad, or virtual keyboard), a cursor control component 1020 (e.g., mouse, pointer, or trackball), and/or a location determination component 1022 (e.g., a Global Positioning System (GPS) device as illustrated, a cell tower triangulation device, and/or a variety of other location determination devices as described above.) In one implementation, the disk drive component 1010 may comprise a database having one or more disk drive components.

In accordance with embodiments of the present disclosure, the computer system 1000 performs specific operations by the processing component 1004 executing one or more sequences of instructions contained in the system memory component 1006, such as described herein with respect to the cable locator device(s), geophysical survey systems, and/or the server device(s). Such instructions may be read into the system memory component 1006 from another computer-readable medium, such as the static storage component 1008 or the disk drive component 1010. In other embodiments, hardwired circuitry may be used in place of or in combination with software instructions to implement the present disclosure.

Logic may be encoded in a computer-readable medium, which may refer to any medium that participates in providing instructions to the processing component 1004 for execution. Such a medium may take many forms, including but not limited to, non-volatile media, volatile media, and tangible media employed incident to a transmission. In various embodiments, the computer-readable medium is non-transitory. In various implementations, non-volatile media includes optical or magnetic disks and flash memory, such as the disk drive component 1010, volatile media includes dynamic memory, such as the system memory component 1006, and tangible media employed incident to a transmission includes coaxial cables, copper wire, and fiber optics, including wires that comprise the bus 1002 together with buffer and driver circuits incident thereto.

Some common forms of computer-readable media include, for example, floppy disk, flexible disk, hard disk, magnetic tape, any other magnetic medium, CD-ROM, DVD-ROM, any other optical medium, any other physical medium with patterns of holes, RAM, PROM, EPROM, FLASH-EPROM, any other memory chip or cartridge, cloud storage, or any other medium from which a computer is adapted to read. In various embodiments, the computer-readable media are non-transitory.

In various embodiments of the present disclosure, execution of instruction sequences to practice the present disclosure may be performed by the computer system 1000. In various other embodiments of the present disclosure, a plurality of the computer systems 1000 coupled by a communication link 1024 to the network 108 (e.g., such as a LAN, WLAN, PTSN, and/or various other wired or wireless networks, including telecommunications, mobile, and cellular phone networks) may perform instruction sequences to practice the present disclosure in coordination with one another.

The computer system 1000 may transmit and receive messages, data, information and instructions, including one or more programs (e.g., application code) through the communication link 1024 and the network interface component 1012. The network interface component 1012 may include an antenna, either separate or integrated, to enable transmission and reception via the communication link 1024. Received program code may be executed by processor 1004 as received and/or stored in disk drive component 1010 or some other non-volatile storage component for execution.

Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the scope of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components, and vice versa.

Software, in accordance with the present disclosure, such as program code or data, may be stored on one or more computer-readable media. It is also contemplated that software identified herein may be implemented using one or more general-purpose or special-purpose computers and/or computer systems, networked and/or otherwise. Where applicable, the ordering of various steps described herein may be changed, combined into composite steps, and/or separated into sub-steps to provide features described herein.

The foregoing is not intended to limit the present disclosure to the precise forms or particular fields of use disclosed. As such, it is contemplated that various alternate embodiments and/or modifications to the present disclosure, whether explicitly described or implied herein, are possible. Persons of ordinary skill in the art in possession of the present disclosure will recognize that changes may be made in form and detail without departing from the scope of what is claimed.

What is claimed is:

1. A method of locating a reflective object comprising:
receiving a first image of a physical environment that includes a reflective object, wherein the first image was captured by an imaging sensor at a first position and a first orientation when a first quantity of light from a light generator illuminates the physical environment during the capture of the first image by the imaging sensor, wherein the imaging sensor and the light generator are housed in a same device;

receiving a second image of the physical environment that includes the reflective object that was captured by the imaging sensor at the first position and the first orientation when a second quantity of light from the light generator that is less than the first quantity of light illuminates the physical environment during the capture of the second image by the imaging sensor, wherein at least some light of the second quantity of light is reflected back to the imaging sensor during the capture of the second image; and comparing the second image to the first image to generate a compared image, wherein the compared image illustrates a difference in illuminance of the reflective object that distinguishes the reflective object from other objects in the physical environment.

2. The method of claim 1, wherein the reflective object is a reflective cable that includes a conductive wire surrounded by an electrically insulating sheath that provides an exterior surface, wherein the reflective cable includes reflective material that is on or visible through the exterior surface and that is configured to reflect a spectrum of light provided by a light source back to the light source.

3. The method of claim 1, wherein the first image is captured when the physical environment has a first ambient illuminance and the second image is captured with the physical environment has a second ambient illuminance.

4. The method of claim 3, wherein the first ambient illuminance and the second ambient illuminance are substantially the same.

5. The method of claim 3, wherein the first ambient illuminance and the second ambient illuminance are greater than 10 lux.

6. The method of claim 3, wherein the first ambient illuminance and the second ambient illuminance is in a range of 0-100,000 lux.

7. The method of claim 3, wherein the first ambient illuminance and the second ambient illuminance is in a range of 10-100,000 lux.

8. The method of claim 1, further comprising:
displaying the compared image on a display device.

9. The method of claim 1, wherein the difference in illuminance of the reflective object in the first image and the second image is visually negligible to a human eye.

10. A method of determining position of a reflective cable, comprising:
imaging, by a cable locator device, a physical environment that includes a reflective cable, wherein the cable locator device includes an imaging sensor that detects light, and wherein a plurality of distances from the cable locator device to the reflective cable are calculated from a three-dimensional model of the physical environment generated using the imaging; and
determining a plurality of positions of the reflective cable based on the plurality of distances and a position of the cable locator device.

11. The method of claim 10, further comprising:
inputting the one or more positions of the reflective cable into a geophysical survey model.

12. The method of claim 10, further comprising:
displaying the one or more positions of the reflective cable on a display device.

13. The method of claim 10, wherein the reflective cable is provided in a geophysical survey system for an electrical survey of a sub-ground of the physical environment.

14. The method of claim 10, wherein the imaging is lidar.

15. The method of claim 10, wherein the imaging is photogrammetry.

16. The method of claim 10, wherein the reflective cable is surrounded by an electrically insulating sheath having a reflective material throughout an entirety of the electrically insulating sheath.

17. A reflective object locator device, comprising:
an imaging sensor;
a light generator;
a non-transitory memory; and
one or more hardware processors coupled to the non-transitory memory and the imaging sensor and configured to read instructions from the non-transitory memory to cause the system to perform operations comprising:
receiving a first image of a physical environment that includes a reflective object, wherein the first image was captured by the imaging sensor at a first position and a first orientation when a first quantity of light from the light generator illuminates the physical environment during the capture of the first image by the imaging sensor;
receiving a second image of the physical environment that includes the reflective object that was captured by the imaging sensor at the first position and the first orientation when a second quantity of light from the light generator that is less than the first quantity of light, but greater than zero, illuminates the physical environment during the capture of the second image by the imaging sensor; and
comparing the second image to the first image to generate a compared image, wherein the compared image illustrates a difference in illuminance of the reflective object that distinguishes the reflective object from other objects in the physical environment.

18. The reflective object locator device of claim 17, wherein the operations further comprise:
calculating one or more distances from the reflective object locator device to the reflective object; and
determining one or more positions of the reflective object based on the one or more distances and a position of the reflective object locator device.

19. The reflective object locator device of claim 18, wherein the operations further comprise:
inputting the one or more positions of the reflective cable into a geophysical survey model.

20. The reflective object locator device of claim 17, further comprising:
a display device coupled to the one or more hardware processors, wherein the operations further comprise:
displaying the compared image on the display device.

* * * * *